(12) United States Patent
Kim

(10) Patent No.: US 7,699,857 B2
(45) Date of Patent: Apr. 20, 2010

(54) HYDRODYNAMIC SUTURE PASSER

(76) Inventor: Andrew Kim, 30213 Del Roy Rd., Temecula, CA (US) 92591

( * ) Notice: Subject to any disclaimer, the term of this patent is extended or adjusted under 35 U.S.C. 154(b) by 1756 days.

(21) Appl. No.: 10/614,653

(22) Filed: Jul. 7, 2003

(65) Prior Publication Data

US 2005/0021052 A1    Jan. 27, 2005

(51) Int. Cl.
*A61B 17/04* (2006.01)
*A61B 17/12* (2006.01)

(52) U.S. Cl. .................................................. 606/144

(58) Field of Classification Search ................ 606/144, 606/139, 148
See application file for complete search history.

(56) References Cited

U.S. PATENT DOCUMENTS

| | | | |
|---|---|---|---|
| 919,138 A | 4/1909 | Drake et al. ................ 606/112 |
| 1,815,725 A | 7/1931 | Pilling et al. |
| 3,470,875 A | 10/1969 | Johnson |
| 3,840,017 A | 10/1974 | Violante .................... 606/112 |
| 3,842,840 A | 10/1974 | Schweizer |
| 3,946,740 A | 3/1976 | Bassett |
| 4,164,225 A | 8/1979 | Johnson et al. |
| 4,224,947 A | 9/1980 | Fukuda ...................... 606/772 |
| 4,312,337 A | 1/1982 | Donohue |
| 4,493,323 A | 1/1985 | Albright et al. .......... 606/5.501 |
| 4,602,635 A | 7/1986 | Mulhollan et al. .......... 606/112 |
| 4,621,640 A | 11/1986 | Mulhollan et al. |
| 4,643,178 A | 2/1987 | Nastari et al. ......... 606/124.103 |
| 4,890,615 A | 1/1990 | Caspari et al. .............. 606/144 |
| 5,152,769 A * | 10/1992 | Baber ........................ 606/145 |
| 5,236,443 A * | 8/1993 | Sontag ....................... 606/224 |
| 5,275,614 A * | 1/1994 | Haber et al. ................ 606/207 |
| 5,350,385 A * | 9/1994 | Christy ....................... 606/139 |
| 5,515,871 A * | 5/1996 | Bittner et al. ............... 128/898 |
| 5,562,683 A | 10/1996 | Chan |
| 5,569,270 A * | 10/1996 | Weng ......................... 606/144 |
| 5,910,148 A | 6/1999 | Reimels et al. |
| 6,022,360 A | 2/2000 | Reimels et al. |

(Continued)

FOREIGN PATENT DOCUMENTS

WO    WO 2004/034867    *    4/2004

(Continued)

OTHER PUBLICATIONS

International Preliminary Report of Patentability for PCT/US2004/021586 filed on Jul. 6, 2004.

*Primary Examiner*—Todd E Manahan
*Assistant Examiner*—Lindsey Bachman
(74) *Attorney, Agent, or Firm*—James W. Chang

(57) ABSTRACT

A hydrodynamic suturing instrument, comprises a elongated cannulated suturing needle having a distal end configured to carry a suture through tissue and a proximal end adapted to connect to a syringe barrel and a lumen extending from said proximal end to an opening at the distal end for having a size for the passage of a suture, and the opening at the distal end configured to receive a suture extending from the lumen along an outer surface of the needle wherein a sharp point extends forward of the suture. A companion instrument includes forceps having a distal end with jaws and a proximal end with a lumen extending from the proximal end to the distal end for passage of the needle, and the jaws having an opening enabling passage of the needle through tissue grasped in the jaws.

5 Claims, 4 Drawing Sheets

U.S. PATENT DOCUMENTS

| | | | |
|---|---|---|---|
| 6,099,550 A * | 8/2000 | Yoon | 606/205 |
| 6,299,590 B1 * | 10/2001 | Luscher et al. | 604/11 |
| 6,440,098 B1 * | 8/2002 | Luscher | 604/57 |
| 6,626,917 B1 * | 9/2003 | Craig | 606/144 |
| 6,702,786 B2 * | 3/2004 | Olovson | 604/198 |
| 7,077,826 B1 * | 7/2006 | Gray | 604/171 |

FOREIGN PATENT DOCUMENTS

| | | |
|---|---|---|
| WO | WO 2005/007201 A2 | 1/2005 |
| WO | WO 2005/007201 A3 | 1/2005 |

* cited by examiner

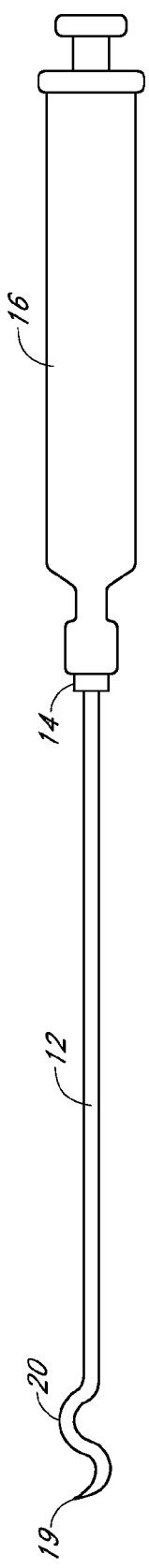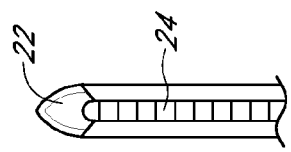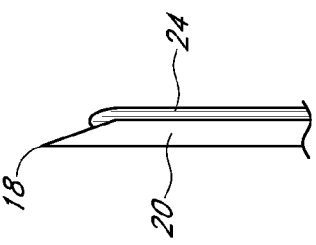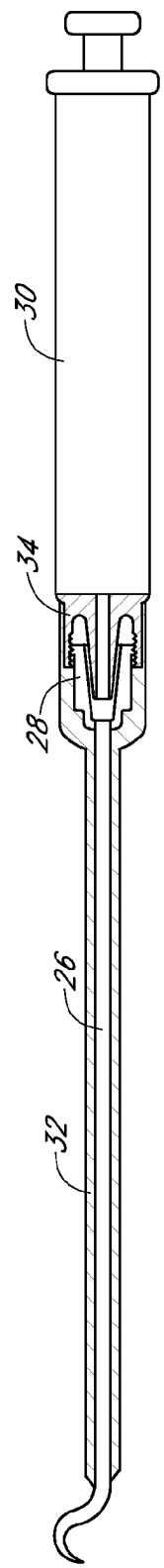
FIG. 1A
FIG. 1B
FIG. 1C
FIG. 2

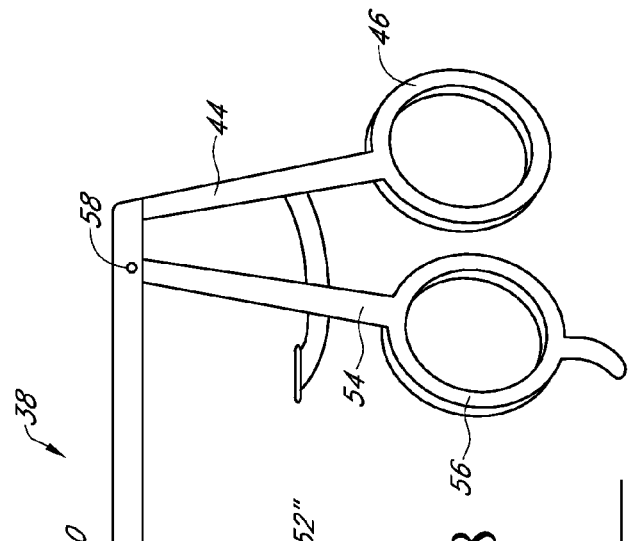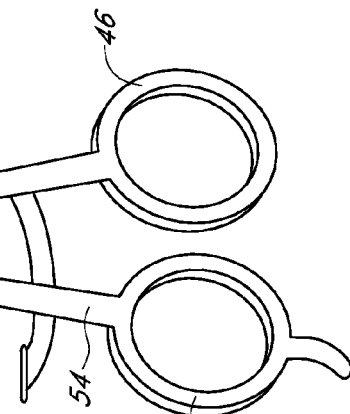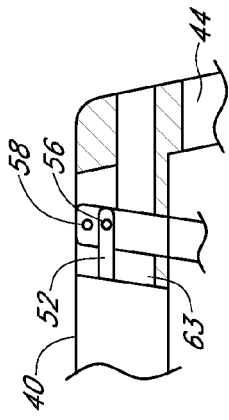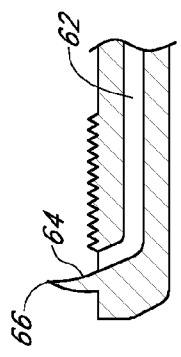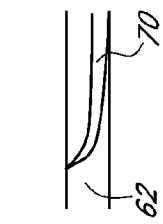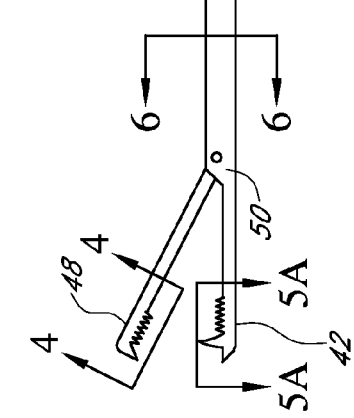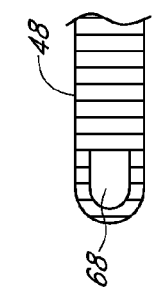

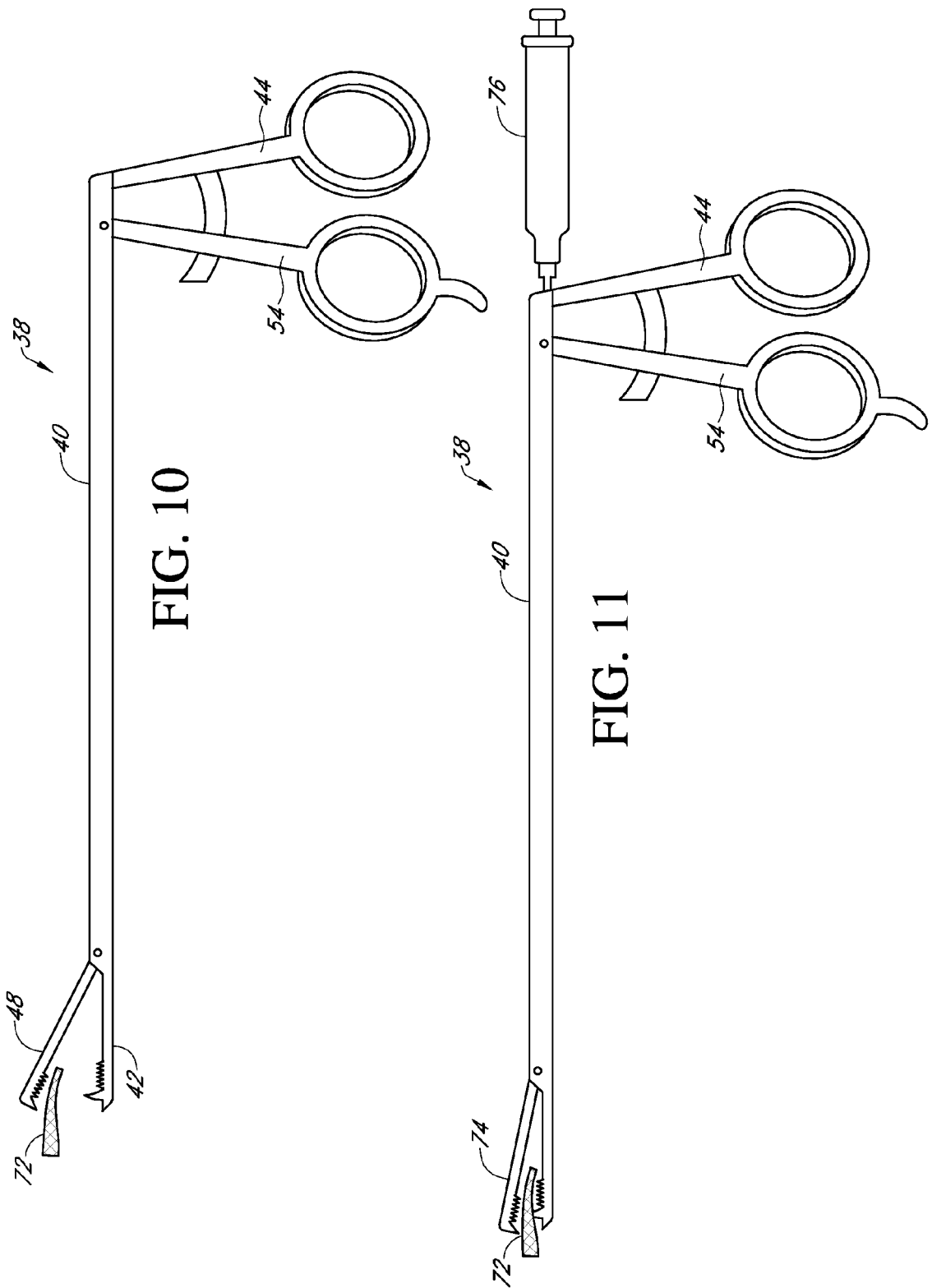

HYDRODYNAMIC SUTURE PASSER

BACKGROUND OF THE INVENTION

The present invention relates to surgical instruments and pertains particularly to an apparatus and method for passing sutures through tissue.

Many surgical techniques are currently carried out in very confined space both by choice and by necessity. Open surgery is seldom used where other techniques such as arthroscopic, endoscopic or laproscopic surgical techniques are available because of the benefits to the patient.

Such techniques reduce the pain and discomfort to the patient and decreases the recovery time and scarring. However, the suturing of tissue under such conditions is difficult with the tools and instruments available today.

While many instruments have been proposed for this problem in the past, such instruments have a number of drawbacks. Presently available instruments or suture passers generally fall in two main categories. One type of device is designed to propel a relatively rigid, usually monofilament, suture with mechanical force through a cannula or hollow needle through the tissue. These devices cannot pass a braided suture through the tissue. Another type of device uses a solid needle or wire with a closed or open eyelet to carry the suture through tissue. The open eyelet may catch on tissue making passage through the tissue difficult. These devices also require other instruments to grasp and pull the free suture from the needle or wire.

A number of the prior art instruments are disclosed in the following patents:

U.S. Pat. No. 4,890,615 to Caspari et al, No. 919,138 to Drake et al, No. 3,840,017 to Violante, No. 4,224,947 to Fukuda, and U.S. Pat. No. 4,643,178 to Nastari et al disclose suturing instruments wherein sutures are passed through hollow needles after the needles penetrate through tissue to be sutured, and having the disadvantage of requiring grasping of the suture material by an instrument not useful in arthroscopic surgery.

U.S. Pat. No. 4,493,323 to Albright et al, and Nos. 4,602,635 and 4,621,640 to Mulhollan et al disclose instruments for internal suturing in confined space, but require multiple instrument manipulation and movement of needles carrying sutures entirely through tissue to be sutured. The Albright et al patent discloses a pair of needles that are forced outwardly through the end of a tube by a plunger to penetrate and extend through the tissue to be sutured to be grasped and pulled by the surgeon to position a suture thread loop attached to the needles. The Mulhollan et al patent U.S. Pat. No. 4,621,640 discloses a curved needle carried by a pivoting head movable to set the needle in the tissue to be sutured. The needle is then released and the instrument withdrawn and another instrument inserted to pull the needle through. Mulhollan et al patent U.S. Pat. No. 4,602,635 discloses an instrument for tying knots in sutures in a manipulation area external of the body after the sutures are passed through the tissue. The knots are then forced into place adjacent the tissue by another instrument.

U.S. Pat. No. 1,815,725 to Pilling et al, No. 3,470,875 to Johnson, No. 3,842,840 to Schweizer, No. 3,946,740 to Bassett and No. 4,164,225 to Johnson et al disclose suturing instruments having pivoted, scissor-like arms with a needle at the end of an arm forced through tissue to be sutured and into the end of another arm where the suture is grasped or clamped. The instruments are of a structural design that is not practical in arthroscopic surgery.

U.S. Pat. No. 4,312,337 to Donohue discloses an instrument for drilling and wiring bones having scissor-like arms carrying cannula sections through which a wire is passed, the wire being cut and tied after the cannula sections are withdrawn. The structure is such that it does not permit the instrument to be used in arthroscopic surgery.

Accordingly there is a need for improved suturing instruments for effective use in close confined spaces.

SUMMARY AND OBJECTS OF THE INVENTION

It is the primary object of the present invention to provide an improved instrument for suturing tissue in confined spaces.

In accordance with a primary aspect of the present invention, a hydrodynamic suturing instrument, comprises an elongated cannulated suturing needle having a distal end configured to pass a suture through tissue, a proximal end adapted to connect to a syringe barrel connector and a lumen extending from said proximal end to an opening at said distal end for the passage of a suture, and said distal end configured with a sharp point extending forward of an opening to said lumen, said opening configured to receive a suture extending from said lumen along an outer surface of said needle wherein said sharp point extends forward of said suture. A suture is loaded into the syringe through the needle by drawing it in with a liquid and expelled from the needle after passage through tissue to pass the suture through the tissue.

An additional aspect of the invention comprises a forceps having a distal end with jaws and a proximal end and a lumen extending from said proximal end to said distal end for passage of said needle, and said jaws having an opening enabling passage of said needle through tissue grasped in said jaws.

BRIEF DESCRIPTION OF THE DRAWINGS

The above and other objects and advantages of the present invention will become apparent from the following description and the accompanying drawings wherein:

FIG. 1A is a side elevation view of a first embodiment of a suture passing instrument in accordance with the invention;

FIGS. 1B-1C is enlarged side and front elevation views respectively of the tip of the needle of FIG. 1A with a suture;

FIG. 2 is a side elevation view of an alternate embodiment of the invention;

FIG. 3A is a side elevation view of another instrument of the invention;

FIG. 3B is a side elevation section view of the proximal end of the instrument of FIG. 3A;

FIG. 4 is a view taken on line 4-4 of FIG. 3A;

FIG. 5A is a view taken on line 5-5 of FIG. 3A;

FIG. 5B is a view taken on line 5B-5B of FIG. 5A;

FIG. 6 is a view taken on line 6-6 of FIG. 3A;

FIG. 7 is a view like FIG. 6 of an alternate embodiment of the instrument of FIG. 3A;

FIG. 8 is a view like FIG. 6 of an alternate embodiment of the instrument of FIG. 3A;

FIG. 9 is a side elevation view of a an alternate needle tip for the instrument of FIG. 1 shown in a passage of the instrument of FIG. 3A;

FIG. 10 is a side elevation view of the instrument of FIG. 3A shown in use.

FIG. 11 is a side elevation view of the instruments of FIG. 3A and FIG. 1 shown in use.

DETAILED DESCRIPTION OF THE PREFERRED EMBODIMENTS

Figure 12A:
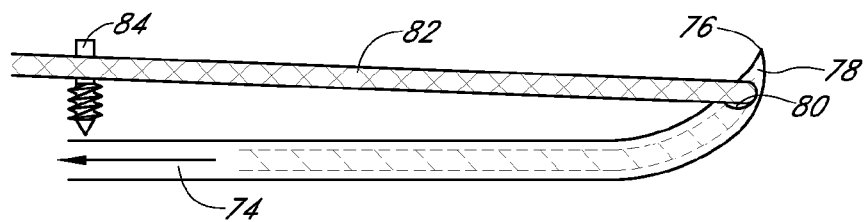
FIG. 12A-12D are enlarged partial views illustrating the loading of the needle and passing of a suture.

Referring to the drawings and particularly to FIGS. 1A-1C a suturing instrument in the form of a special needle and syringe combination is illustrated and designated generally by the numeral 10. The needle 12 is selected or formed as a cannula with a lumen of sufficient size to receive the desired size suture and having a luer lock fitting 14 on a proximal end to connect to a traditional syringe barrel 16. The syringe barrel may be of a conventional construction or have an outer surface configured with a shape, such as hexagonal or other, for easy grip and manipulation. A distal or outer end of needle 12 is formed with a penetrating tip 18 and a portion 20 configured for ease of passing through tissue in a confined space. In the illustrated embodiment the end of the needle is formed substantially as a cork screw with a substantially helical configuration to enable easier manipulation and passage of the needle tip through tissue in a confined space. The tip has an opening 22 of sufficient size for passage of a suture 24 through the lumen and to the exterior where it folds over an edge of the opening and extends along the outer surface of the needle body as shown in FIGS. 1B and 1C. Opening 22 is configured to enable the easy passing of a suture and the application of some force to the suture by the trailing edge of the opening without cutting the suture. In some instances, a trailing edge or portion of the opening away from the tip where the suture folds over may require rounding or notching to eliminate a sharp edge to prevent damage to the suture. The distal or tip end of the needle may have any number of configurations including straight, curved, hooked or cork screw as illustrated to enable it to be easily manipulated to pass through tissue.

As shown in FIG. 1B the end of suturing needle 12 is cut at an angle providing a forward most sharp point or tip 18 for penetration of flesh. An opening 22 of the lumen of the cannula is formed by an angled cut of the end of the cannula positioning opening 22 to one side of and aft of the forwardly extending sharp point 18. This opens the lumen to one side so that sharp tip 18 is positioned or extends forward of the opening and the portion of the suture coming out of the opening. The trailing edge of the opening 22 is rounded or has a rounded radius so that it will not cut the suture and will enable it to slide smoothly over the edge into or out of the opening. Opening 22 is configured to enable the passage of a suture 24 along the lumen and out the passage where it folds over and extends along an outside surface of the suturing needle. Any sharp edge at the trailing edge of the lumen should be removed to avoid cutting or damaging the suture.

Syringe 16 is of conventional construction with a barrel and piston or plunger and functions in the present instrument to draw a length of suture hydro dynamically into the needle and to expel it after the suture needle is passed through a selected tissue. This is accomplished by inserting an end of a suture into the opening 22 at the end of the needle, submerging opening 22 of the needle in water or another suitable liquid and drawing the syringe plunger back to draw a length of the suture and a quantity of liquid into the barrel of the syringe. A length of suture is drawn by the hydraulic force of the liquid into and through the needle and in most instances into the barrel of the syringe. The needle tip with suture is then passed through a portion of tissue and the suture then expelled from the end of the needle and syringe by hydraulic pressure upon depressing the plunger. The suture then extends through the tissue with opposite ends available to grasp and tie off. Additional or successive passages of the suture through the tissue are accomplished in the same manner until sufficient stitching is achieved.

Needle 12 may vary in length and gauge or diameter depending upon the requirements of the situation. Certain surgical locations require a longer needle to reach the suture site. The needle and syringe is selected to have a needle lumen of sufficient size to receive a length of suture of the desired size and the syringe to have sufficient capacity to accommodate the length and size of suture. Where the length of the needle is such that flexibility may become a problem, it may be stiffened by a sleeve as illustrated in FIG. 2.

In operation, a length of suture is selected and an end of it is inserted into the end of the needle attached to the syringe. The end of the needle with suture is submerged in a quantity of liquid and liquid and suture is drawn into the syringe by drawing the plunger back. The suture is carried up the tip and barrel of the cannulated needle and syringe by the hydrodynamic pressure resulting from the suction force generated by pulling the syringe plunger outward. The needle loaded with the suture is inserted in an opening in the body and passed through the tissue to be sutured and the suture expelled from the needle by hydraulic force by depressing the plunger of the syringe. Thus, the suture is passed through the tissue by a combination of a needle and hydraulic force from the liquid in the syringe.

It will be appreciated that the suture can be loaded in the needle in any suitable manner. For example, one end of the suture may be inserted into the needle at the connector end prior to connecting to the syringe. The other end of the syringe loaded in the syringe and the syringe loaded with a liquid. The needle may then be connected to the liquid loaded syringe and a portion expelled from the needle prior to passing the needle though tissue.

As illustrated in FIG. 2, a needle 26 is formed in the usual manner with a curved or hook tip and a luer lock connector 28 for coupling to a syringe 30 in the usual manner. Needle 26 is covered by a stiffening sleeve 32 which extends along the length of the needle from the connector to the syringe to a position where the distal end is curved. Stiffening sleeve 32 is also preferably formed with a suitable connector to mate with a second or outer surface on the syringe body. This connector may be a luer lock connector or other type connector. The sleeve adds sufficient stiffening to a long needle to enable it to be more easily manipulated in the suturing process. The needle and stiffening sleeve may be made of the same or different material. They may also be made simultaneously.

The suturing needle may be used alone or in conjunction with other available instruments such as forceps or other grasping tools. It may also be used in combination with a forceps type instrument as illustrated in FIG. 3 and designate generally by the numeral 38. The instrument comprises an elongated barrel 40 having a fixed or stationery jaw 42 at a distal end and a fixed handle 44 with a thumb ring 46 at a proximal end. A moveable jaw 48 is pivotally mounted by a pin 50 at the distal end above or opposite fixed jaw 42 and is operated by a rod 52 (FIG. 3B) connected through a bore 60 in barrel 40 and connected to a moveable handle 54. Moveable handle 54 has a finger ring 56 and is pivotally mounted by a pin 58 at the proximal end of member 40. Actuating rod 52 extends along a bore 60 extending the length of barrel 40 and is moveable by means of moveable handle 54 to open and close upper jaw 48. A second bore or cannula 62 extends axially along the length of barrel 40 to receive a suture needle at the proximal end and exits at an upward angle along a surface 64 of an upward extending wedge projection 66 on lower jaw 42. Bore 62 has a vertically oriented circular opening so that it can receive and guide a needle having a bent tip as shown in FIG. 9. The tip of the needle is preferably bent upward so that when it engages wedge surface 64 it is further biased upward through a tissue in the forceps.

Opening 62 preferably has a side opening 63 to enable side release or removal of a suture. The surface projection 64 on wedge projection 66 guides the tip of a suture needle upward through a tissue that clamped in the jaws of the forceps. Upper jaw 48 has an opening 68 as shown in FIG. 4 for passage of a tip and portion of the outer end of a suturing needle and a suture. The surface of the jaw is formed with cross grooves or ridges to enhance grip on tissue or a suture or the like.

Referring to FIG. 7, an alternate barrel construction is illustrated with a barrel 40' having an actuating rod passage 60 same as in the FIG. 6. embodiment. A needle passage 62' has a closed oval configuration without a side slot for passage of a suture. FIG. 8, illustrates a configuration having two actuating rod passages for two actuating rods 52". A needle cannula may be incorporated or formed in the elongated support member, as above, or it may be a separate cannula mounted below and extending along the member. The cannula would curve upward and extend through the lower jaw at the distal end.

FIG. 9 illustrates a side view of the needle passage with a curved needle 70 therein. The tip of the needle is curved to one side and positioned within the passage so that it is oriented with the needle tip up. The oval configuration of the passage will receive a curved tip needle in one of two orientations and maintain its orientation as it passes through the passage or cannula. This positions the tip so that it is guided through tissue grasped in the jaws of the forceps.

Referring to FIG. 10 forceps 38 is illustrated in use in the process of grasping a pieces of tissue 72 to be sutured. The tissue may be within a confined space accessible through a small opening or through a tube or cannula. In use the forward end of the forceps is inserted through an opening and tissue to be sutured is grasped between jaws 42 and 48. A suture is prepared by selecting a needle 74 of the appropriate length and configuration and attached to a syringe 76. The needle is selected to have a length sufficient to pass through the cannula or passage in the forceps from the proximal end to the distal end and extend through the tissue. A portion of the suture is loaded into the end of the needle as discussed above. The needle is then passed through the cannula and through the tissue in the forceps. The suture is then expelled from the end of the needle by hydraulic force from pushing the plunger of the syringe forward. The end of the suture is then available to grasp with a suitable tool and tie off or pass again through the tissue.

Figure 12B:
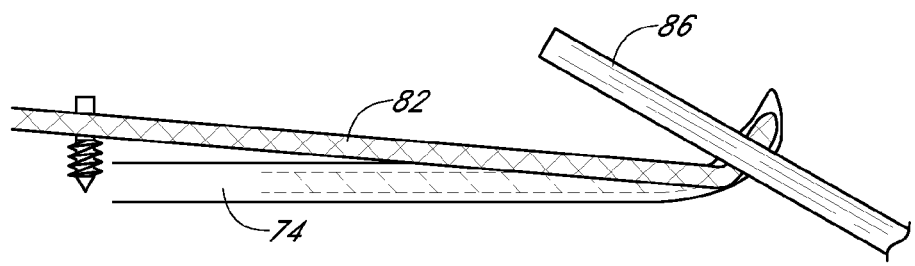
Figure 12C:
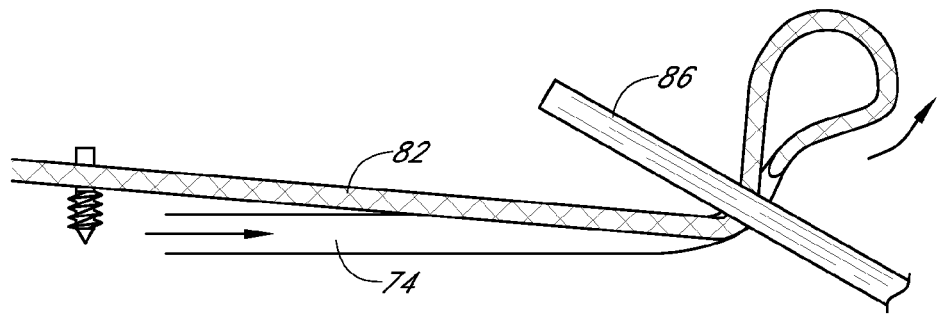
Figure 12D:
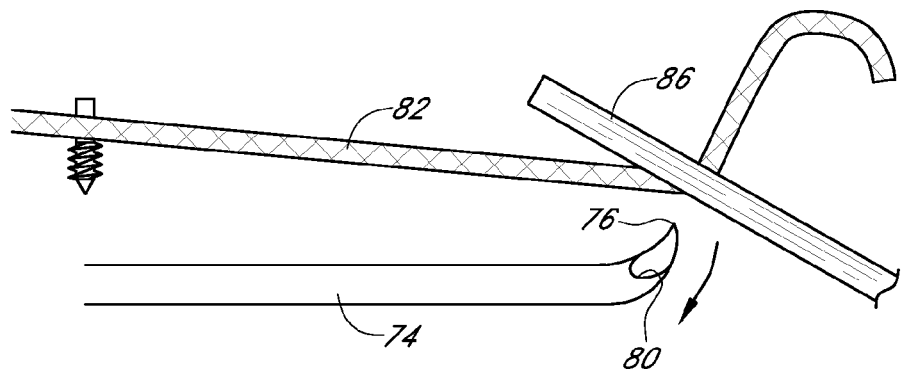

As shown in FIGS. 12A-12D a hollow needle or cannula 72 is illustrated having a hook or an upturned tip at its distal end with a sharp point 76. An opening 78 into the cannula cuts across the canula forming a generally oval opening with a sharp tip or point 76 projecting forward of the opening and a trailing edge 80 that is aft of the opening. The trailing or aft edge 80 of the opening is formed with a radius to enable the smooth passage of a suture over it without cutting it. A length of suture 82 is selected and may be secured by an anchor screw 84 to a bone structure (not shown) A free end of the suture is inserted into the end of the needle. The end of the needle with suture is submerged in a quantity of liquid and liquid and suture is drawn into the syringe as shown. The suture is carried up the tip and barrel of the cannulated needle and syringe by the hydrodynamic pressure resulting from the suction force generated by pulling the syringe plunger outward. The needle loaded with the suture is inserted into and passed through the tissue to be sutured as in FIG. 12A. Once the tip of the needle and opening has passed through the tissue, the plunger of the syringe is pressed forward expelling the suture by hydraulic force from the end of the needle as in FIG. 12C. The needle is then withdrawn and the free end of the suture can be grasped by forceps or other tool and tied off or reintroduced through the tissue as needed. This procedure is repeated until suturing is completed.

While I have illustrated and described my invention by means of specific embodiments, it is to be understood that numerous changes and modifications may be made therein without departing from the spirit and the scope of the invention as shown in the appended claims.

I claim:

1. A method for suturing comprising the steps of:
   providing an elongate needle having a distal end and a proximal end and a lumen extending from said proximal end to said distal end having sufficient size for passage of a predetermined size suture, said distal end having a tip configured for passage with a suture through a tissue;
   providing a syringe detachably connected to said needle proximal end;
   selecting and introducing a length of suture into at least said needle from outside of said syringe and said needle; wherein said step of selecting and introducing a length of suture into at least said needle comprises inserting an end of said suture into said distal end of said needle; submerging said distal end of said needle with said suture in a quantity of liquid; and drawing said length of suture and a quantity of liquid into said needle with said syringe;
   drawing a quantity of liquid through said distal end of said needle so as to further draw said length of suture towards said syringe;
   passing said distal end of said needle with said suture through a tissue to be sutured; and
   expelling said length of suture from said distal end of said needle by hydraulic force from a quantity of said liquid in said syringe.

2. A method for suturing according to claim 1 wherein said needle is provided to have a curved configuration at said distal end.

3. A method for suturing according to claim 1 wherein said needle is provided to have a stiffening cover over a major portion of said needle.

4. A method for suturing according to claim 1 further comprising the steps of:
   providing an elongate tubular member having a distal end and a proximal end and a passage extending from said proximal end to said distal end, first and second jaws on said distal end disposed in opposed relation, one of said first and second jaws being movable relative to the other and having an opening there through, the other of said first and second jaws including an open end of said passage oriented toward said opening, and means at said proximal end for moving said moveable jaw between open and closed positions;
   providing said elongate needle of sufficient length to extend said distal end thereof through said passage past said open end and through said opening in said one of said jaws; and
   grasping a tissue to be sutured between said first and second jaws; and
   extending a said distal end thereof through said passage past said open end through said tissue and through said opening in said one of said jaws.

5. A method for suturing according to claim 4 wherein said needle is provided to have a curved configuration at said distal end; and said passage having an oval configuration to accommodate and maintain said curved needle oriented.

* * * * *